United States Patent
Armand et al.

(10) Patent No.: US 6,841,638 B2
(45) Date of Patent: Jan. 11, 2005

(54) IONIC COMPOUNDS WITH DELOCALIZED ANIONIC CHARGE, AND THEIR USE AS ION CONDUCTING COMPONENTS OR AS CATALYSTS

(75) Inventors: Michel Armand, Montréal (CA); Christophe Michot, Grenoble (FR); Yurii Yagupolskii, Kiev (UA); Lev Yagupolskii, Kiev (UA); Andrej Bezdudny, Kiev (UA); Natalya Kondratenko, Kiev (UA)

(73) Assignees: ACEP Inc., Montreal (CA); Universite de Montreal, Montreal (CA); Centre National de la Recherche Scientifique, Paris (FR); Institute of Organic Chemistry National Academy of Sciences of Ukraine, Kiev (UA)

( * ) Notice: Subject to any disclaimer, the term of this patent is extended or adjusted under 35 U.S.C. 154(b) by 25 days.

(21) Appl. No.: 10/366,450

(22) Filed: Feb. 14, 2003

(65) Prior Publication Data

US 2004/0162362 A9 Aug. 19, 2004

Related U.S. Application Data

(62) Division of application No. 09/931,076, filed on Aug. 17, 2001, now Pat. No. 6,548,567, which is a division of application No. 09/269,264, filed as application No. PCT/FR98/01663 on Jul. 27, 1998, now Pat. No. 6,340,716.

(30) Foreign Application Priority Data

Jul. 25, 1997 (CA) .............................................. 2211465

(51) Int. Cl.$^7$ ...................... C07C 317/00; C07C 291/00; C07C 311/00; C08F 30/04; C08G 75/30
(52) U.S. Cl. ...................... 526/240; 526/241; 528/388; 556/13; 556/52; 556/58; 556/70; 556/87; 556/112; 556/121; 556/136; 556/140; 556/400; 568/11; 568/30
(58) Field of Search ................................. 526/240, 241; 528/388; 568/11, 30, 27, 28; 556/13, 52, 58, 70, 87, 112, 121, 136, 140, 400; 564/82; 521/25; 429/188; 502/159, 200, 216

(56) References Cited

U.S. PATENT DOCUMENTS

| | | | |
|---|---|---|---|
| 4,026,783 A | * | 5/1977 | Grot ........................... 204/266 |
| 5,256,821 A | | 10/1993 | Armand |
| 5,350,646 A | | 9/1994 | Armand et al. |
| 5,446,134 A | | 8/1995 | Armand et al. |
| 5,463,005 A | | 10/1995 | Desmarteau |
| 5,538,812 A | * | 7/1996 | Lee et al. ................... 429/307 |
| 5,554,664 A | | 9/1996 | Lamanna et al. |
| 5,683,832 A | | 11/1997 | Bonhote et al. |
| 5,698,369 A | | 12/1997 | Kawamura et al. |
| 5,731,123 A | | 3/1998 | Kawamura et al. |
| 5,827,602 A | | 10/1998 | Koch et al. |
| 6,008,265 A | | 12/1999 | Vallee et al. |
| 6,008,267 A | | 12/1999 | Vallee et al. |
| 6,025,457 A | | 2/2000 | Ohno et al. |
| 6,114,083 A | | 9/2000 | Kawamura et al. |
| 6,136,500 A | | 10/2000 | Kobayashi et al. |
| 6,143,460 A | | 11/2000 | Kobayashi et al. |
| 6,423,467 B1 | * | 7/2002 | Kawauchi et al. ....... 430/270.1 |

FOREIGN PATENT DOCUMENTS

| | | |
|---|---|---|
| EP | 0 834 502 A2 | 4/1998 |
| EP | 0 850 920 A2 | 7/1998 |

OTHER PUBLICATIONS

Levchenko et al., Journal of Organic Chemistry of the USSR, vol. 4, No. 1, pp 144–148, Jan. 1968.
Van Leusen et al., Recueil Des Travaux Chimiques Des Pays–Bas, vol. 103, No. 2, pp 41–45, Feb. 2, 1984, XP002086723.
Chemical Abstracts, vol. 54, No. 20, XP002086725, Oct. 25, 1960.
Burk et al., Journal of Computational Chemistry, vol. 17, No. 1, pp 30–41, 1996, XP002086724.
Yagupol'skii et al., "Trifluoromethylsulfonylimino and Bis-(trifluoromethylsulfonylimino) Derivatives of Arenesulfonic Acids," Russian Journal of Organic Chemistry, vol. 31, No. 6, pp. 691–695, 1995.

* cited by examiner

*Primary Examiner*—Susan Berman
(74) *Attorney, Agent, or Firm*—Burns, Doane, Swecker & Mathis, L.L.P.

(57) ABSTRACT

The invention relates to an ionic compound corresponding to the formula $[R^1X^1(Z^1)\text{—}Q^-\text{—}X^2(Z^2)\text{—}R^2]_m\ M^{m+}$ in which $M^{m+}$ is a cation of valency m, each of the groups $X^i$ is $S=Z^3$, $S=Z^4$, $P\text{—}R^3$ or $P\text{—}R^4$; Q is N, $CR^5$, CCN or $CSO_2R^5$, each of the groups $Z^i$ is $=O$, $=NC\equiv N$, $=C(C\equiv N)_2$, $=NS (=Z)_2R^6$ or $=C[S(=Z)_2R^6]_2$, each of the groups $R^i$, is Y, YO—, YS—, $Y_2N$— or F, Y represents a monovalent organic radical or alternatively Y is a repeating unit of a polymeric frame.

The compounds are useful for producing ion conducting materials or electrolytes, as catalysts and for doping polymers.

4 Claims, No Drawings

IONIC COMPOUNDS WITH DELOCALIZED ANIONIC CHARGE, AND THEIR USE AS ION CONDUCTING COMPONENTS OR AS CATALYSTS

This application is a divisional of application Ser. No. 09/931,076, filed Aug. 17, 2001, now U.S. Pat. No. 6,548,567, which is a divisional of application Ser. No. 09/269,264 filed Mar. 25, 1999, now U.S. Pat. No. 6,340,716, which is a 371 national stage application of PCT/FR98/01663, filed Jul. 27, 1998.

BACKGROUND OF THE INVENTION

FIELD OF THE INVENTION

The present invention relates to ionic compounds comprising a highly delocalized anionic charge, to a process for their preparation and to their uses.

It is well known that the salts of strong acids such as $HClO_4$, $HBF_4$, $HPF_6$ and $HR_FSO_3$ ($R_F$=perfluororadical) have properties in the field of electrochemistry and catalysis, but these properties are limited. The "superacids" obtained by adding a Lewis acid such as $SbF_5$ to the abovementioned compounds are moreover known. However, these compounds are not stable other than in protonated form and in non-solvating media such as aliphatic hydrocarbons. The salts are unstable in the usual polar solvents.

Perfluorosulfonimide derivatives $H[R_FSO_2NSO_2R_F]$ ($R_F$=perfluoroalkyl) have been studied since quite recently. They have advantageous stability properties in protonated form or in the form of salts and are used as solutes in electrochemistry and as catalysts. However, it is not possible to give these salts all of the properties required for all the applications, in particular in terms of acidity, dissociation or solubility, since the use of compounds containing perfluoro chains of several carbons only slightly increases the acidity or the dissociation of the salts, when compared with the simplest compound $R_F=CF_3$, and induces rigidity in the molecule to the detriment of the conductivity properties. Long fluoro chains are both hydrophobic and oleophobic and do not allow any appreciable increase in the solubility in organic media. Replacement of the groups $R_F$ in the simple imides with non-perfluoro or only partially fluorinated groups reduces the acidity and the solubility substantially.

The aim of the present invention is to provide novel ionic compounds derived from perfluorosulfonimides in which the delocalization of the anionic charge is improved, thus resulting in markedly better acidity and dissociation than those of the known compounds, while at the same time retaining good stability.

SUMMARY OF THE INVENTION

Accordingly, a subject of the present invention is ionic compounds, their uses and a process for preparing them.

One compound according to the invention is an ionic compound corresponding to the formula

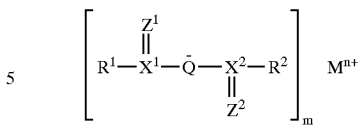
(I)

in which:

$M^{m+}$ is a proton or a metal cation having the valency m, chosen from ions of alkali metals, of alkaline-earth metals, of transition metals or of rare-earth metals, or an organic onium cation or an organometallic cation, $1 \leq m \leq 3$;

$X^1$ and $X^2$, denoted below by $X^i$, represent, independently of each other, $S=Z^3$, $S=Z^4$, $P-R^3$ or $P-R^4$;

Q represents N, $CR^5$, CCN or $CSO_2R^5$;

$Z^1$, $Z^2$, $Z^3$ and $Z^4$, denoted below by $Z^i$, represent, independently of each other, $=O$, $=NC \equiv N$, $=C(C \equiv N)_2$, $=NS(=Z)_2R^6$ or $=C[S(=Z)_2R^6]_2$, Z having the same meaning as $Z^i$, it being understood that, in a segment $-X^1-Q-X^2-$, not more than 3 groups $Z^i$ represent $=O$;

$R^1$, $R^2$, $R^3$, $R^4$, $R^5$ and $R^6$, denoted below by $R^i$, represent, independently of each other, Y, YO—, YS—, $Y_2N$— or F;

Y represents a monovalent organic radical, preferably containing from 1 to 16 carbon atoms, chosen from alkyl, alkenyl, oxaalkyl, oxaalkenyl, azaalkyl, azaalkenyl, aryl, alkylaryl or perfluoroalkyl radicals, or from the radicals obtained from the abovementioned radicals by substitution, in the chains and/or the aromatic part, with hetero atoms such as halogens, oxygen, nitrogen, sulfur or phosphorus; it being understood that sulfur or phosphorus are present, they can optionally be linked to substituted oxygen or nitrogen atoms, or alternatively Y is a repeating unit of a polymeric frame.

When $M^{m+}$ is a metal cation, it can be an alkali metal (in particular $Li^+$ and $K^+$), an alkaline-earth metal (in particular $Mg^{++}$, $Ca^{++}$ or $Ba^{++}$), a transition metal (in particular $Cu^{++}$, $Zn^{++}$ or $Fe^{++}$) or a rare-earth metal (in particular $Re^{+++}$).

When $M^{m+}$ is an onium cation, it can be chosen from ammonium ions $[N(Y^j)_4]^+$, amidinium ions $RC[N(Y^j)_2]_2^+$, guanidinium ions $C[N(Y^j)_2]_3+$, pyridinium ions $[C_5N(Y^j)_6]^+$, imidpazolium ions $C_3N_2(Y^j)_5^+$, imidazolinium ions $C_3N_2(Y^j)_7^+$, triazolium ions $C_2N_3(Y^j)_4^+$, carbonium ions $C_5(Y^j)_5C^+$, $NO^+$ (nitrosyl) or $NO_2^+$ ions, sulfonium ions $[S(Y^j)_3]^+$, phosphonium ions $[P(Y^j)_4]^+$ and iodonium ions $[I(Y^j)_2]^+$. In the various abovementioned onium ions, the substituents $Y^j$ on the same anion can be identical or different. They represent, independently of each other, H or one of the substituents indicated above for Y.

When $M^{m+}$ is an organometallic cation, it can be chosen from metalloceniums. For example, mention may be made of the cations derived from ferrocene, from titanocene, from zirconocene, from an indocenium or from an arene metallocenium. It can also be chosen from metal cations coordinated by atoms such as O, S, Se, N, P or As, borne by organic molecules, in particular in the form of carbonyl, phosphine or porphyrine ligands optionally containing chirality. $M^{m+}$ can also be a cation derived from the alkyl groups defined for Y above and limited to those containing from 1 to 10. carbon atoms, for example a trialkylsilyl, tetraalkylgermanyl or dialkylstannyl derivative; in this case, M is linked to the group $[R^1-X^i(Z^1)-Q^--X^2(Z^2)-R^2]$ via a very labile covalent bond and the compound behaves like a salt. The cation M+ can also be the repeating unit of a conjugate polymer in cationic oxidized form. As specific examples, mention may be made of the methylzinc, phenylmercury, trialkyltin or trialkyllead, chloro[ethylenebis(indenyl)] zirconium(IV) or tetrakis-(acetonitrile)palladium(II) cations. The organometallic cation can form part of a polymer chain.

The compounds according to the invention in which at least one of the groups $X^i$ represents a phosphorous group are particularly advantageous for the great stability of the P—N and P—C bonds and for their flexibility. As a result, these compounds are more soluble and have a lower melting point than the sulfur-containing homologous compounds. Moreover, a large number of phosphorous compounds bearing two substituents R are commercially available or can readily be synthesized. For example, mention may be made of the compounds

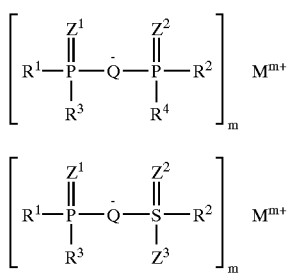
(II)
(III)

Mention may be made in particular of the phosphorous compounds in which Q represents N.

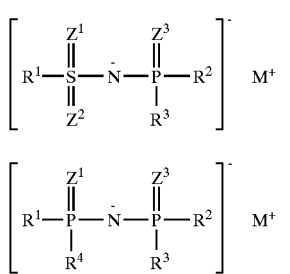
(IV)
(V)

The compounds in which the radicals $Z^i$ represent $R_F SO_2 N$ and those in which the radicals $R^i$ represent a perfluoro group or an alkyl group are particularly advantageous, especially for the high acidity and the dissociation of the corresponding salts.

DETAILED DESCRIPTION OF THE PREFERRED EMBODIMENT

Among the compounds of the present invention corresponding to formula (I), mention may be made of those in which the groups $X^i$ represent $S-Z^i$, more particularly those in which Q is N, and which correspond, respectively, to the formulae:

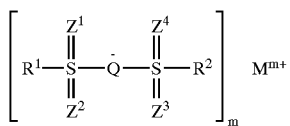
(VI)

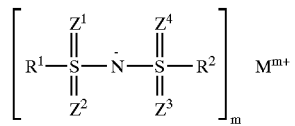
(VII)

One particular family of compounds according to the invention corresponds to formula (VII), given that if $R^1$ is $CF_3$, $R_2$ is a phenyl optionally bearing a halogen or an $NO_2$, three substituents $Z^i$ represent O and one substituent $Z^i$ represents $=NSO_2CF_3$, then M is other than an alkali metal cation or a proton.

Another family of compounds according to the invention corresponds to formula (I) in which the radicals $R^1$ and $R^2$ are chosen, independently of each other, from perfluoroalkyl radicals preferably containing from 1 to 8 carbon atoms, alkyl radicals preferably containing from 1 to 8 carbon atoms, alkenyl radicals preferably containing from 2 to 18 carbon atoms, dialkylamino radicals in which the alkyl radicals preferably contain from 1 to 18 carbon atoms, and styrenyl radicals. For example, mention may be made of the compounds corresponding to the following formulae, in which $R_f$ represents a perfluoro radical, Q and M have the meaning given above, and Y, Y', Y'', Y''' and Y'''' have the meaning given above for Y:

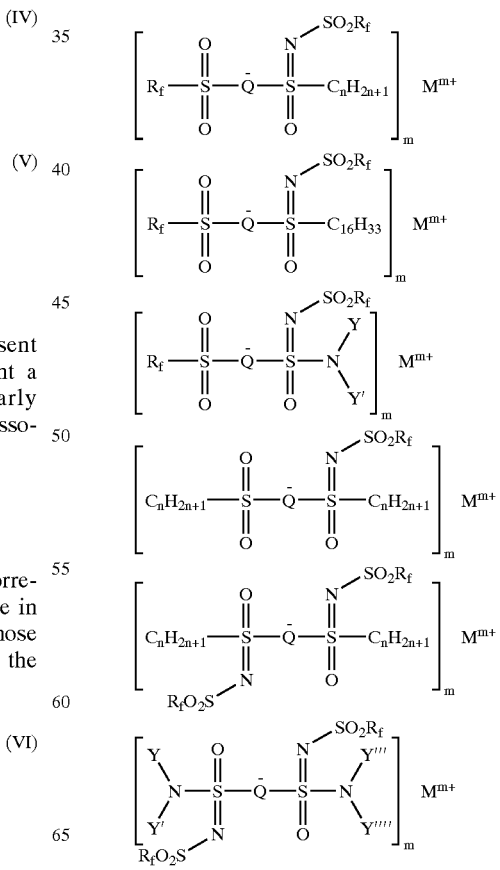

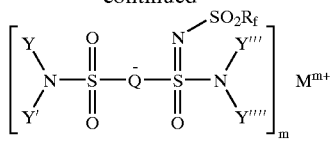

The compounds corresponding to formula (I), in which the groups $Z^i$ are chosen from $=O$, $=N—C\equiv N$ and $=C(C\equiv N)_2$, constitute another advantageous family. The presence of one or more groups $=N—C\equiv N$ or $=C(C\equiv N)_2$, makes it possible to increase the dissociation and the resistance to oxidation of the anion without substantially increasing its molar mass or its volume. For example, mention may be made of the following compounds:

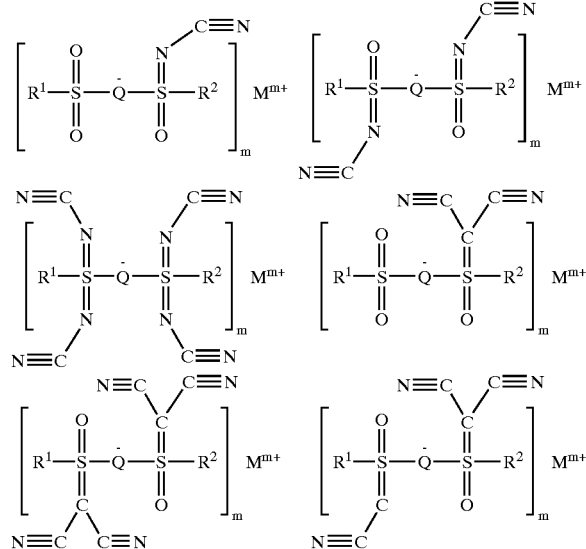

Mention may also be made in particular of the compounds corresponding to the formula (IV)

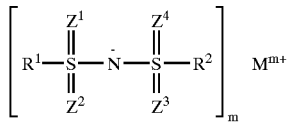

in which three groups $Z^1$ to $Z^3$ represent oxygen and $Z^4$ represents $=C[S(=Z)_2R^6]_2$. For example, mention may be made of the following compounds:

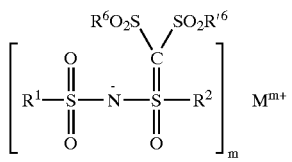

Mention may also be made of the compounds corresponding to the formula

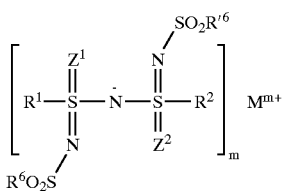

in which the groups $R^i$, $Z^i$ and Q have the meaning given above, in particular compounds in which the groups $Z^i$ are O, and Q is N.

Mention may also be made of the compounds of formula

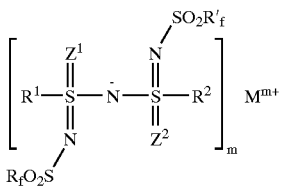

in which the groups $R_f$ and $R'_f$ represent perfluoroalkyl radicals, the groups $Z^i$ and $R^i$ have the meaning given above, in particular compounds in which the groups $Z^i$ are O, and $R_f$ is $CF_3$.

In general, the replacement of the oxygen in the $SO_2$ end groups of

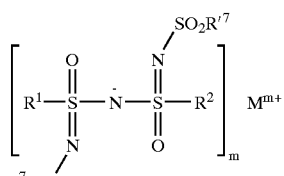

with groups Z representing $=NSO_2R^i$ makes it possible to construct molecules of general formula:

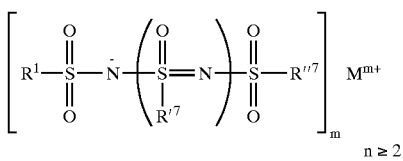

$n \geq 2$

The choice of the substituents $R^i$ in the compounds of the present invention makes it possible to obtain compounds in which the anion has intrinsic chirality on a sulfur atom. Such compounds are useful for inducing enantiomeric selectivity during the preparation of active organic compounds or for inducing stereoselectivity in polymerization reactions. Among these compounds, mention may be made of those corresponding to one or other of the following formulae $[R^1SO_2N—S^*=O(R^2)=NSO_2R^6]^-$ in which $R^1$ is different from $R^6$, or $[R^1SO_2N—S^*=O(R^2)=N—S^*=O(R^5)=NSO_2R^6]^-$. The compounds most particularly preferred are those in which $R^1$ and $R^6$ represent, independently of each other, a radical chosen from F, $CF_3$, $C_2F_5$, $C_4F_9$, $C_6F_{13}$ and $C_8F_{17}$, and $R^2$ and $R^5$ represent, independently of each other, an alkyl, an aryl, an alkylaryl or a dialkylamino preferably containing from 1 to 20 carbon atoms.

The ionic compounds of the present invention can be prepared by various processes.

In general, a compound corresponding to the formula

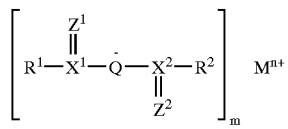

is prepared by reacting a precursor compound, noted below $(Z^1,L)$ comprising the group $Z^1$ and a leaving group L, with a derivative $A^2Z^2$ of the group $Z^2$ according to one of the following reaction schemes:

$R^1—X^1(Z^1)—Q—X^2(L)R^2+A^2Z^2 \Rightarrow [R^1—X^1(Z^1)—X^2(L)(Z2)R^2]A^+LA$ or $R^1—X^1(Z^1)—QA_2+L—X^2(Z^2)R^2 \Rightarrow [R^1—X^1(Z^1)—X^2(L)(Z_2)R^2]^+ A^-+LA$.

A represents an alkali metal, a proton, an amino or phosphorus-containing base, a trialkylsilyl group, a dialkylstannyl group, MgL1, ZnL1, CdL1, Cu, Mg, Zn, Cd, Hg or a trialkylsilyl, trialkylgermanyl or trialkylstannyl group.

The leaving groups L or L1 are advantageously chosen from halogens, pseudohalogens including fluoro or nonfluoro sulfonates, and imidazoyl, triazolyl and benzotriazoyl radicals.

The compounds $(Z^1,L)$ in which the leaving group is a halogen can be prepared, for example, by the action of a halogenating agent on a salt $R^1—X^1(Z^1)—Q—X^2(O)(R^2)^- A^+$ or on the corresponding acid. The cation A is preferably chosen from alkali metal cations, inorganic ammonium ions $NH_4^+$ or organic ammonium ions $R^3NH^+$ (including pyridinium) and the $Ag^+$ ion, which has strong affinity for Cl, Br and I.

Among the halogenating agents which are useful, mention may be made of $SF_4$, trifluoro(diethylamino)sulfur IV (DAST), thionyl chloride, oxalyl chloride, oxalyl fluoride, phosphorus pentachloride, the mixture $P\Phi_3+CCl_4$, (chloromethylene)dimethylammonium chloride $[CH(Cl)=N(CH_3)_2]^+Cl^-$ or its homologue derived from N-methylpyrrolidinone, and 1-methyl-2-fluoropyridinium iodide. The preparation of a compound $(Z^1,L)$ in which the leaving group is a halogen is illustrated schematically by the following example:

$[CF_3SO_2NSO_2(C_4H_9)]Na+(COCl) \Rightarrow CO+CO_2+[CF_3SO_2NSO(C_4H_9)Cl]+NaCl$ The precursor compounds $(Z^1,L)$, in which the leaving group is imidazolyl, triazolyl or benzotriazolyl, can be obtained by the action of their alkaline salt, their trimethylsilyl derivative or their dimethylstannyl derivative on the corresponding halogenated precursor compound, for example according to the following reaction scheme:
$[CF_3SO_2NSO(C_4H_9)]Cl]+ImSi(CH_3)_3 \Rightarrow ClSi(CH_3)_3+[CF_3SO_2NSO(C_4H_9)Im]$, in which Im represents

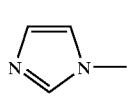 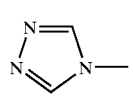 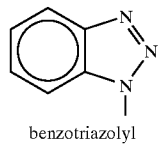

imidazolyl    triazolyl    benzotriazolyl

The precursor compounds $(Z^1,L)$, in which the leaving group is a pseudohalogen such as a sulfonate, can be obtained by the action of the acid chloride or the anhydride of the sulfonic acid corresponding to the sulfonate, on an abovementioned salt $R^1—X^1(Z^1)—Q—X^2(O)R^{2-}M^+$. The reaction of a silver salt with a sulfonyl chloride $R^7SO^2Cl$ ($R^7$ being of the same nature as the groups $R^i$) according to the following scheme is particularly advantageous:

$R^1—X(Z^1)—Q—X(O)R^{2-}Ag^++R^7SO_2Cl \Rightarrow R^1—X(Z^1)—Q—X(SO_3R^7)R^2+AgCl$ In general, it is advantageous to prepare the precursor compounds $R^1—X^1(Z^1)—Q—X^2(L)R^2$ from a compound comprising an anion in which the sulfur or the phosphorus are in the oxidation state IV and III, respectively. On oxidizing these anions, the sulfur VI or phosphorus V derivatives are obtained according to the reaction scheme $R^1—X(Z^1)—Q—X^2(R^2)^-A^++2L \Rightarrow R^1—X(Z^1)—Q—X^2(L)R^2+LA$ The preferred compounds for L are halogens, such as fluorine, chlorine or bromine.

The various leaving groups can be exchanged by techniques that are well known to those skilled in the art. For example, the chlorine can be replaced with fluorine by the action of an agent containing active fluoride ions and an affinity for the chlorine ions, such as silver fluoride AgF or tetramethylammonium fluoride, 1,1,1,3,3,3-hexakis (dimethylamino)-diphosphazenium fluoride $\{[(CH_3)_2N]_3P\}_2N^+F^-$ or tetrakis(tris(dimethylamino)-phosphoranylidene-aminophosphonium fluoride $\{[(CH_3)_2N]_3P=N\}_4P^+F^-$ or the compound of addition of tris(dimethylamino)sulfonium fluoride with trimethylfluorosilane $[(CH_3)_2N]_3S^+[Si(CH_3)_3F_2]^-$.

The imidazole or triazole derivatives can be obtained by the action of their alkaline salt or their trimethylsilyl or dimethylstannyl derivative) on the corresponding derivative, according to the reaction scheme:

$[CF_3SO_2NSO(C_4H_9)Cl]+ImSi(CH_3)_3 \Rightarrow ClSi(CH_3)_3+[CF_3SO_2NSO(C_4H_9)Im]$ in which Im represents imidazolyl, triazolyl or benzotriazolyl.

A symmetrical compound, in which $X^1(Z^1)$ is identical to $X^2(Z^2)$, can be prepared by the action of an ionic nitride or a metallic derivative of hexamethyl-disilazane or of ammonia in the presence of a base on a precursor containing a leaving group L, according to the following reaction scheme, in which R, X and Z have the meaning given above, respectively, for $R^i$, $X^i$ and $Z^i$, A and L are as defined above:
$2RX(Z)L+A_3N \Rightarrow [RX(Z)]_2N^-A^++2LA$. For example:

$2CF_3SO(=NSO_2CF_3)F+Li_3N \Rightarrow [CF_3SO(=NSO_2CF_3)]_2N^-A^++2LiF$

The nitriding agent may advantageously be $Li_3N$, ammonia, its derivatives with silanes and their alkali metal derivatives such as $N[SiCH_3)_3]_2Li$, $N[SiCH_3)_3]_2Na$, and $N[SiCH_3)_3]_2K$.

A compound of formula $[R^1SO_2N—S^*=O(R^2)=NSO_2R^3]^-M^+$ can be obtained by reacting a salt $[R^1SO_2NSO_2R^2]^-M'^+$ with a halogenating agent, to give the precursor $R^1SO_2NSOR^2(X)$ (X being a halogen). Said precursor is then condensed with a sulfonamide $R^3SO_2NH_2$ in the presence of a base or with its metallic derivatives such as $R^3SO_2NLi_2$ or $R^3SO_2NNa_2$. The desired cation for the final compound is obtained by standard ion-exchange processes.

In the same way, the ionic carbides allow the compounds $[RX(Z)]_3C^-A^+$ to be prepared, according to the reaction scheme $2RX(Z)L+A_4C \Rightarrow [RX(Z)]_3C^-A^++3LA$.

Given the large possible choice for the substituents which can be present on the anionic group, the compounds of the invention make it possible to induce ionic conduction properties in most organic, liquid or polymeric media containing polarity, even low polarity. The applications are important in the field of electrochemistry, in particular for the storage of energy in primary or secondary generators, in supercapacitors, in fuel cells and in electroluminescent diodes. The compatibility of the ionic compounds of the invention with organic liquids or polymers makes it possible to induce pronounced antistatic properties, even when the content of ionic compound is extremely low. Accordingly, another subject of the present invention consists of an ion conducting material consisting of an ionic compound of the present invention dissolved in a solvent.

The ionic compound used to produce an ion conducting material is preferably chosen from compounds whose cation is ammonium, or a cation derived from a metal, in particular lithium or potassium, zinc, calcium, rare-earth metals, or an organic cation, such as a substituted ammonium, an imidazolium, a triazolium, a pyridinium or a 4-dimethylaminopyridinium, said cations optionally bearing a substituent on the carbon atoms of the ring. The ion conducting material thus obtained has high conductivity and high solubility in solvents, on account of the weak interactions between the positive charge and the negative charge. It has a broad field of electrochemical stability, and it is stable in both reducing and oxidizing media. Furthermore, the compounds which have an organic cation and a melting point below 150° C., in particular the compounds containing an imidazolium, triazolium, pyridinium or 4-dimethylaminopyridinium cation, have high intrinsic conductivity, even in the absence of solvent, when they are in the molten state.

The solvent for an ion conducting material of the invention can be an aprotic liquid solvent, a solvating polymer, a polar polymer or a mixture thereof. The aprotic liquid solvent is chosen, for example, from linear ethers and cyclic ethers, esters, nitriles, nitro derivatives, amides, sulfones, sulfolanes, alkylsulfamides and partially hydrogenated hydrocarbons. The solvents which are particularly preferred are diethyl ether, dimethoxyethane, glyme, tetrahydrofuran, dioxane, dimethyltetrahydrofuran, methyl or ethyl formate, propylene or ethylene carbonate, alkylcarbonates (in particular dimethylcarbonate, diethylcarbonate and methyl propyl carbonate), butyrolactones, acetonitrile, benzonitrile, nitromethane, nitrobenzene, dimethylformamide, diethylformamide, N-methylpyrrolidone, dimethyl sulfone, tetramethylene sulfone, tetramethylene sulfone and tetraalkylsulfonamides containing from 5 to 10 carbon atoms.

The solvent for the ion conducting material can be a polar polymer chosen from solvating, crosslinked or non-crosslinked polymers, bearing or not bearing grafted ionic groups. A solvating polymer is a polymer which contains solvating units containing at least one hetero atom chosen from sulfur, oxygen, nitrogen and fluorine. As examples of solvating polymers, mention may be made of polyethers of linear, comb or block structure, forming or not forming a network, based on poly(ethylene oxide), or polymers containing the ethylene oxide or propylene oxide or allyl glycidyl ether unit, polyphosphazenes, crosslinked networks based on polyethylene glycol crosslinked with isocyanates or networks obtained by polycondensation and bearing groups which allow the incorporation of crosslinkable groups. Mention may also be made of block copolymers in which certain blocks bear functions which have redox properties. Needless to say, the above list is not limiting, and any polymer with solvating properties can be used.

An ion conducting material of the present invention can simultaneously comprise an aprotic liquid solvent chosen from the aprotic liquid solvents mentioned above and a polar polymeric solvent comprising units containing at least one hetero atom chosen from sulfur, nitrogen, oxygen and fluorine. It can comprise, from 2 to 98% of liquid solvent. As examples of such a polar polymer, mention may be made of polymers mainly containing units derived from acrylonitrile, from vinylidene fluoride, from N-vinylpyrrolidone or from methyl methacrylate. These polymers can bear ionic groups. The proportion of aprotic liquid in the solvent can range from 2% (corresponding to a plasticized solvent) to 98% (corresponding to a gelled solvent). An ion conducting material of the present invention can also contain a salt conventionally used in the prior art for the production of an ion conducting material. Among the salts which can be used as a mixture with an ionic compound according to the invention, the salt most particularly preferred is chosen from perfluoroalkane sulfonates, bis(perfluoroalkylsulfonyl) imides, bis(perfluoroalkylsulfonyl)methanes and tris (perfluoroalkylsulfonyl)methanes.

Needless to say, an ion conducting material of the invention can also contain the additives conventionally used in this type of material, and in particular inorganic or organic fillers in powder or fibre form.

An ion conducting material of the invention can be used as an electrolyte in an electrochemical generator. Another subject of the present invention is thus an electrochemical generator comprising a negative electrode and a positive electrode which are separated by an electrolyte, characterized in that the electrolyte is an ion conducting material as defined above. Preferably, the cation of the ionic compound of the electrolyte is $Li^+$ or $K^+$. According to one specific embodiment, such a generator comprises a negative electrode consisting of lithium metal, or an alloy thereof, optionally in the form of a manometric dispersion in lithium oxide, or a nitride double salt of lithium and of a transition metal, or an oxide of low potential having the general formula $Li_{1+y}Ti_{2-x/4}O_4$ ($0 \leq x$, $y \leq 1$), or carbon and carbon-based products derived from the pyrolysis of organic materials. When the negative electrode functions by exchanging lithium ions, it is particularly advantageous to use, for the electrolyte, a compound of the invention in which the cation is an $Li^+$ ion. According to another embodiment, the generator comprises a positive electrode chosen from vanadium oxides $VO_x$ ($2 \leq x \leq 2.5$), $LiV_3O_8$, $Li_yNi_{1-x}Co_xO_2$, ($0 \leq x$, $y \leq 1$), magnesium spinels $Li_yMn_{1-x}M_xO_2$, (M=Cr, Al, V, Ni, $0 \leq x \leq 0.5$; $0 \leq y \leq 2$), organic polydisulfides, FeS, $FeS_2$, iron sulfate $Fe_2(SO_4)_3$, iron and lithium phosphates and phosphosilicates of olivine structure, or their products of substitution of the iron with manganese, which are used alone or as mixtures. The positive electrode collector is preferably made of aluminum.

An ionic compound of the present invention can also be used to induce an ionic conductivity in media of low polarity, such as aliphatic and aromatic hydrocarbons and media which contain a large fraction thereof, polymers of relatively unpolar and/or hydrophobic nature, and supercritical carbon dioxide.

An ion conducting material of the present invention can also be used in a supercapacitor. Another subject of the present invention is, consequently, a supercapacitor using at least one carbon electrode with a high specific surface, or an electrode containing redox polymer, in which the electrolyte is an ion conducting material as defined above.

The ionic compounds of the present invention can be used for doping polymers in order to improve their electron conduction. The polymers concerned are essentially polyacetylenes, polyphenylenes, polypyrrols, polythiophenes, polyanilines and polyquinolines which are substituted or unsubstituted, as well as polymers in which the aromatic units are separated by the vinylene unit —CH=CH—. The doping process consists in partially oxidizing the polymer in order to create carbocations whose charge is compensated by the anions in the compounds of the invention. This doping can be carried out chemically or electrochemically, optionally simultaneously with the formation of the polymer. For this specific application, compounds of the invention bearing a highly delocalized charge are preferably chosen, in particular the compounds in which Z is =C(C≡N)$_2$=NSO$_2$R or =C(SO$_2$R)$_2$, which impart thermal and mechanical stability properties. The polymers thus doped are another subject of the present invention.

In addition, an ion conducting material of the present invention can be used as an electrolyte in an electrochromic device. An electrochromic device in which the electrolyte is an ion conducting material according to the invention is another subject of the present invention. Such a device also comprises electrodes whose active material is chosen from WO$_3$, MoO$_3$, iridium oxyhydroxides IrO$_x$H$_y$, (2≦x≦3; 0≦y≦3), Prussian blue, viologens and their polymers, and aromatic polyimides.

The compounds of the present invention can be used for the catalysis of various types of chemical reaction, and in particular for polymerization reactions, condensation reactions, addition or elimination reactions, oxidation or reduction reactions, solvolyses, Friedel-Crafts reactions and Diels-Alder reactions. For these applications in catalysis, the compounds will be chosen essentially as a function of the cation associated with the anionic part.

For the catalysis of Diels-Alder reactions or Friedel-Crafts reactions, the cations of an alkali metal, of an alkaline-earth metal, of a transition metal or of a rare-earth metal are suitable. Compounds containing an H$^+$, Li$^+$, Mg$^{++}$, Ca$^{++}$, Cu$^{++}$, Zn$^{++}$, Al$^{+++}$, Fe$^{++}$ or Fe$^{+++}$ cation are preferred.

The compounds of the invention in which the cation is an onium of the diazonium, sulfonium, iodonium or metallocenium type can be used as cationic polymerization initiators, in particular for polymerizing or crosslinking vinyl ethers, epoxides, acetals and cyclic ethers, vinylamides, oxazolines, isobutylene, styrene or siloxanes. Under the action of actinic radiation, such compounds generate the corresponding acidic form which is capable of initiating a cationic polymerization reaction. A compound of the invention can be used as a photoinitiator optionally in the presence of a sensitizer, or of a radical initiator which can be initiated thermally or by actinic radiation. The compounds of the invention in the form of an amine salt can serve as initiators for cationic polymerizations by heating to release the corresponding protonic form. Similarly, if the cation is a salt of a cationic azo compound (for example as represented below), it can serve, by heating, as an initiator for radical polymerizations.

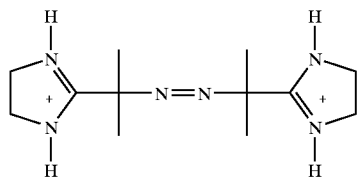

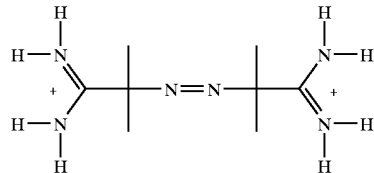

The present invention makes it possible to obtain compounds in which the anion has intrinsic chirality, which makes it possible to induce enantiomeric asymmetry during the use of said compounds as catalysts, to prepare stereoregular polymers and to give the materials containing them an optical rotation.

The present invention is explained in further detail by means of the examples which follow, which describe the preparation and various uses of compounds of the invention. However, the invention is not limited to these examples.

EXAMPLE 1

The compound of sulfur in the state IV [CF$_3$SO$_2$NS(O)CF$_3$]$^-$Na$^+$ was prepared according to one or other of the two possible reaction schemes:

CF$_3$S—SCF$_3$+CF$_3$SO$_2$NCl$_2$⇒CF$_3$SO$_2$NS(Cl)CF$_3$+CF$_3$SCl

CF$_3$SO$_2$NS(Cl)CF$_3$+NaOS(CH$_3$)$_3$⇒[CF$_3$SO$_2$NS(O)CF$_3$]$^-$Na$^+$+ClSi(CH$_3$)$_3$  a)

or

CF$_3$SO$_2$NNa$_2$+CF$_3$SO$_2$Cl⇒[CF$_3$SO$_2$NS(O)CF$_3$]$^-$Na$^+$+NaCl  b)

The halogenated compound CF$_3$SO$_2$NS(Cl)CF$_3$ was prepared by chloridation of the sodium salt [obtained via one of the routes a) or b)] in the absence of solvent and converted into the fluoro derivative by the action of N(CH$_3$)$_4$F in ether at −35° C.

2.67 g of the halogenated compound CF$_3$SO$_2$NS(F)CF$_3$ in 20 ml of THF were reacted with 170 mg of lithium nitride to give the salt:

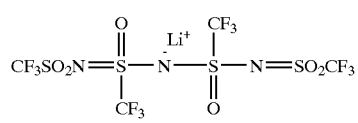

EXAMPLE 2

15.6 g of butanesulfonyl chloride were dissolved in 100 ml of anhydrous acetonitrile to which were added 14.9 g of trifluoromethanesulfonamide and 20.4 g of 1,4-diazabicyclo-2,2,2-octane (DABCO). The mixture was stirred for 4 hours at room temperature and the DABCO hydrochloride formed was then removed by centrifugation and the solvent was evaporated off. The solid residue was taken up in 100 ml of a saturated solution of KCl in water to which were added 15 ml of acetic acid. The precipitate of [C$_4$H$_9$SO$_2$NSO$_2$CF$_3$]$^-$K$^+$ was filtered off and purified by crystallization from hot water.

9.22 g of the salt obtained above were dissolved in 50 ml of anhydrous acetonitrile, to which were added 2.6 ml of oxalyl chloride (COCl)$_2$ and three drops of DMF acting as catalyst. After the evolution of gas ceased, 4.4 g of trifluoromethanesulfonamide and 6.73 g of DABCO were added. After stirring at room temperature, the DABCO hydrochloride formed was removed by centrifugation and the solution was poured into 100 ml of water containing 15% by weight of KCl and 15 ml of acetic acid. The precipitate was separated out, washed with water and recrystallized from ethanol. It corresponds to the formula:

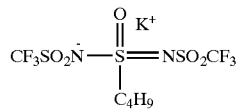

The reaction scheme for the successive steps of the process is as follows:

$[C_4H_9SO_2NSO_2CF_3]^-K^+ + (COCl)_2 \Rightarrow KCl + C_4H_9SO(Cl)NSO_2CF_3$ $C_4H_9SO(Cl)NSO_2CF_3 + 2N(C_2H_4)_3N \Rightarrow N(C_2H_4)_3NHCl + [C_4H_9SO(NSO_2CF_3)NSO_2CF_3]^-N(C_2H_4)_3NH^+$ $[C_4H_9SO(NSO_2CF_3)NSO_2CF_3]^- - N(C_2H_4)_3NH^+ + KCl$
$\Rightarrow N(C_2H_4)_3NHCl +$ $[C_4H_9SO(NSO_2CF_3)NSO_2CF_3]^-K^+$.

EXAMPLE 3

5 g of the salt of Example 2 were treated with 1.17 g of lithium tetrafluoroborate in isopropanol. The $KBF_4$ precipitate was filtered off and the lithium salt was obtained by evaporation of the solvent and drying under vacuum at 60° C.

1 g of polyethylene oxide of mass $10^6$ was dissolved in 30 ml of acetonitrile with 834 mg of the lithium salt. The solution was evaporated in a PTFE ring so as to form a 200 µm film. This film is amorphous according to the differential calorimetry study, and has a conductivity of greater than $2.10^{-5}$ $Scm^{-1}$ at 25° C.

EXAMPLE 4

6 ml of a 10M solution of butyllithium in hexane were added to 8.97 g of nonafluorobutanesulfonamide in 25 ml of ether at −25° C., followed by addition of 4.13 g of bis (trifluoromethyl)trichlorophophorane $P(CF_3)Cl_3$. The lithium chloride was removed by filtration and the salt:

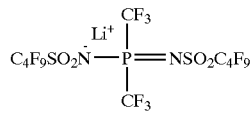

was purified by recrystallization from dioxane and treatment of the solvate under vacuum at 80° C. This salt is soluble in relatively non-polar solvents such as ethyl carbonate (dielectric constant of 2.8) to form a solution which has a conductivity of greater than $4.10^{-3}$ $Scm^{-1}$ and an anodic oxidation stability of +5.5 V vs. $Li^°:Li^+$.

EXAMPLE 5

The compound $[C_8H_{17}SO_2NSO_2CF_3]^-K^+$ was prepared by a procedure similar to that of Example 2, using octanesulfonyl chloride. 36.3 g of this compound were dissolved in anhydrous DMF and 13 g of (chloromethylene) dimethylammonium chloride $[CH(Cl)=N(CH_3)_2]^+Cl^-$ were added. A precipitate of KCl was formed and was removed by filtration. 1.7 g of lithium nitride were added to the solution. After stirring for 24 hours at room temperature, the reaction product was centrifuged and the supernatant was poured into 200 ml of water saturated with potassium chloride. The pasty precipitate was separated out after settling had taken place and was washed several times with water and then extracted with 50 ml of an equivalent-volume mixture of diethoxy-2-ethane and dichloromethane. After evaporation of the solvent, a hydrophobic salt was obtained, having the formula:

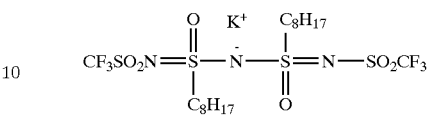

This compound, either in the initial form of the potassium salt, or in the form of the lithium salt obtained by ion-exchange, has pronounced surfactant and lubricant properties, and it is soluble in solvents with a low dielectric constant, in particular in aromatic hydrocarbons. In these two forms, Li or K salt, the compound facilitates the extrusion of homo- and copolymers based on ethylene oxide for the preparation of ion conducting films, as well as for the preparation of composite electrodes in which the active material is an insertion compound which can be used for the manufacture of electrochemical generators.

EXAMPLE 6

253 g of polyaniline protonated in chloride form were suspended in acetonitrile and 6.7 g of the compound of Example 5 were added. The mixture was stirred for 24 hours and the polymer, in which the chloride ions were exchanged with the ion $(CF_3SO_2NSOC_8H_{17})_2N^-$, was washed with water and with ethanol to remove the KCl, then dried. The conjugate polymer in conductive doped form is soluble in solvents of low polarity such as xylenes, dichloroethane or chloroform. The conductivity of the polymer is greater than 1 $Scm^{-1}$ and stable with respect to atmospheric agents, in particular moisture.

It has anticorrosion properties. It especially allows ferrous metals to be protected against corrosion.

EXAMPLE 7

The ionic compound $[CF_3SO_2NSO_2(3,5-C_6H_3(CF_3)_2]^-K^+$ was prepared by a method similar to that of Example 2, starting with 3,5-bis(trifluoromethyl)benzenesulfonyl chloride and trifluoromethanesulfonamide. 18.6 g of salt were treated with 7 g of DAST $(C_2H_5)_2NSF_3$. The fluoro compound obtained:

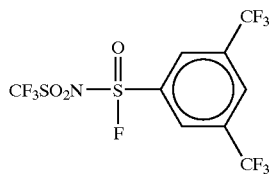

was purified by distillation under vacuum. 4.27 g of this compound were added to 30 ml of anhydrous THF containing 670 mg of malonotrile and 18 mg of lithium hydride. At the end of the reaction, observed by the end of the release of hydrogen, the reaction mixture was filtered and the THF was evaporated off. The solid residue was taken up in water and filtered off. 4.4 g of brucine sulfate in 50 ml of water were added and the reaction mixture was stirred for 24 hours. After separation and drying, 8 g of the precipitate formed were treated with a solution of 1.6 g of a solution of sodium tetraphenylborate in 20 ml of an equivalent-volume, water/ethanol solution. After filtration, the solution was dried to give the sodium salt of the anion, which is intrinsically chiral at its sulfur atom, resolved into an active isomer with brucine:

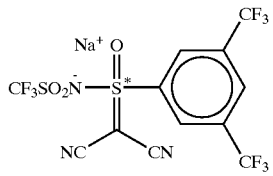

The lithium, magnesium or rare-earth metal and yttrium salts of this anion induce enantiomeric excesses of from 50 to 92% during the catalysis of Diels-Alder reactions and aldol condensations. A cationic-polymerization catalyst was prepared by the action of acetyl chloride in stoichiometric amount on the silver salt, which was itself obtained by exchanging the sodium salt with silver toluene sulfonate in an isopropanol/toluene mixture. This catalyst induces a polymerization of propylene oxide into an optically active polymer. In a similar manner, methyl vinyl ether is polymerized into a water-insoluble crystalline isotactic macromolecule, in contrast with the polymers obtained with non-chiral cationic initiators. The compounds:

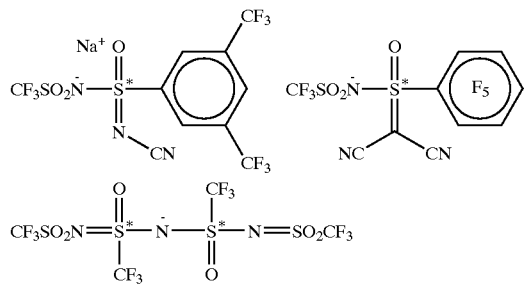

also have intrinsic chirality at the anionic centre, allowing the catalysis of reactions favouring an enantiomer, the polymerizations giving polymers which are optically active or which exhibit tacticity.

EXAMPLE 8

The compound [(C$_4$H$_9$SO$_2$)$_2$N]Na was prepared according to the method of Runge et al. (Chem. Ber. 88-4, 533 (1955)) and halogenated with thionyl chloride in acetonitrile, the reaction being catalyzed by DMF. The chloride C$_4$H$_9$SO$_2$NSO(Cl)C$_4$H$_9$ dissolved in THF was treated with ammonia so as to form the sulfimidosulfamide C$_4$H$_9$SO$_2$NSO(NH$_2$)C$_4$H$_9$. Equimolar amounts of the chloride and the amide were reacted in pyridine to form the pyridinium salt:

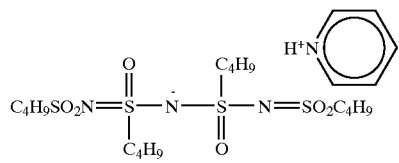

The salt of the rhodamine dye 6G of this anion was precipitated by simple mixing in water of rhodamine 6G perchlorate and of the pyridinium salt. This salt has pronounced solubility in a large number of organic solvents, in particular in monomers such as methyl methacrylate or (styrene, and this solubility is maintained during the polymerization of these monomers. The solid solutions thus formed are highly fluorescent and allow the preparation of solid lasers, as thin films or as fibres.

EXAMPLE 9

Bis(indenyl)zirconium dichloride was treated with the silver salt of the compound of Example 6 to give the compound:

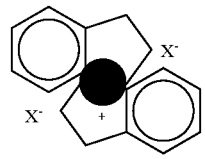

in which X$^-$ is [CF$_3$SO$_2$NSOC$_8$H$_{17}$]$_2$N$^-$.

This metallocene has excellent solubility in the usual polymerization solvents such as toluene or aliphatic hydrocarbons, and it shows appreciable activity for the polymerization of α-olefins, in particular for ethylene and propylene.

EXAMPLE 10

0.14 g (4.12 mmol) of Li$_3$N and 0.04 g (0.33 mol) of 4-dimethylaminopyridine as catalyst were added, under argon, to a solution of 2.43 g, (8.25 mmol) of N-(trifluoromethylsulfonyl)phenylsulfonimidoyl fluoride prepared according to the method described by Garlyauskajte et al. (Tetrahedron, vol. 50, p. 6891, 1994) in 4 ml of anhydrous THF. The reaction medium was then refluxed for 24 hours. After cooling and evaporation of the solvent under vacuum, the residue obtained was dissolved in 10 ml of water and the solution was filtered and then passed through an Amberlite IR-120 ion-exchange column (acidic form). 50% of potassium hydroxide solution was added to this solution. The precipitate formed was separated out, recrystallized from water and then dried by azeotropic distillation with benzene. The compound below was thus obtained:

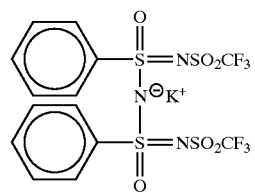

The corresponding lithium salt was obtained by ionic exchange with lithium chloride in THF. Concentrated solutions of this lithium salt in ether are activated for the catalysis of Diels-Alder reactions.

EXAMPLE 11

2.83 g (10 mmol) of N-(trifluoromethylsulfonyl) trifluoromethylsulfonimidoyl fluoride, prepared according to the method described in Example 1, dissolved in 4 ml of anhydrous THF were added to a solution of 174 mg of Li$_3$N (10 mmol) in 4 ml of anhydrous THF, followed by addition of 0.04 g (0.33 mmol) of 4-dimethylaminopyridine as catalyst. The reaction mixture was then stirred for 24 hours. After evaporation of the solvents under vacuum, the residue obtained was taken up in saturated KCl solution. The precipitate formed was separated out, recrystallized from water and then dried by azeotropic distillation with benzene. The compound below was thus obtained:

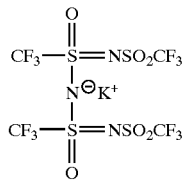

According to the same process, starting with [C$_4$F$_9$SO$_2$NSOC$_4$F$_9$]$^-$Na$^+$, the compound below was obtained:

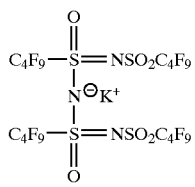

EXAMPLE 12

22.44 g (200 mmol) of 1,4-diazabicyclo[2.2.2]octane (DABCO) dissolved in 20 ml of anhydrous tetrahydrofuran at 0° C. were added to a solution, at 0° C. and under argon, of 14.36 g (100 mmol) of sulfamoyl chloride (CH$_3$)$_2$NSO$_2$Cl (sold by Aldrich) and 14.91 g of trifluoromethanesulfonamide CF$_3$SO$_2$NH$_2$(100 mmol), prepared according to the procedure of Example 2, in 60 ml of anhydrous tetrahydrofuran. After 2 hours at 0° C., the reaction was continued for 24 hours at room temperature. The DABCO hydrochloride precipitate was removed by filtration on a sinter funnel of porosity No. 4. After evaporation of the tetrahydrofuran and drying, the product was dissolved in 25 ml of ethanol. 9.81 g (100 mmol) of potassium acetate CH$_3$COOK were then added and the precipitate obtained was then recrystallized from refluxing ethanol. After cooling, filtration and drying, the potassium salt (CH$_3$)$_2$NSO$_2$NKSO$_2$CF$_3$ was recovered. 50 mmol of this salt were dissolved in 30 ml of THF and then treated with 50 mmol of oxalyl chloride. A precipitate of potassium chloride formed rapidly, and was removed by filtration. 5 mmol of Li$_3$N were then added, under argon, to the (CH$_3$)$_2$NS(Cl)O=NSO$_2$CF$_3$ solution. After stirring for 72 hours, the solvent was evaporated off and the residue was recrystallized from a solution saturated with potassium chloride. The compound below was obtained:

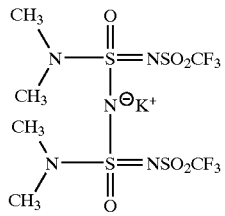

According to the same process, the compound below was obtained by replacing the sulfamoyl chloride with butanesulfonyl chloride:

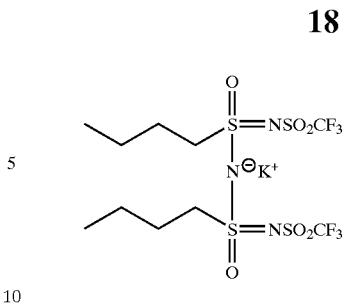

EXAMPLE 13

20 mmol of the sodium salt of sulfonimide [(CH$_3$)$_2$NSO$_2$]$_2$NNa were treated with 20 mmol of thionyl chloride SOCl$_2$ in 10 ml of anhydrous acetonitrile. A precipitate of sodium chloride formed rapidly, concomitantly with formation of (CH$_3$)$_2$NSO(Cl)=NSO$_2$N (CH$_3$)$_2$. After stirring for one hour, 20 mmol of CF$_3$SO$_2$NNa$_2$, prepared beforehand by treating trifluoromethanesulfonamide with sodium methoxide in methanol, were added under argon. After, stirring for 24 hours, the reaction medium was filtered and the solvent was then evaporated off. After passage through a cation-exchange column, the compound below was obtained:

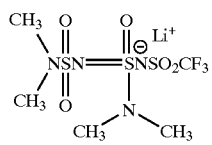

EXAMPLE 14

10 mmol of p-styrenesulfonamide, 0.04 g (0.33 mmol) of dimethylaminopyridine as catalyst and then 0.1 mmol of tert-butylhydroxyquinone were added, under argon, to 10 mmol of N-(trifluoromethylsulfonyl)trifluorosulfonimidoyl fluoride prepared according to the method described in Example 1, dissolved in 10 ml of anhydrous pyridine. The reaction medium was then stirred for 24 hours at 40° C. After evaporation of the pyridine under vacuum, the residue obtained was taken up in THF and then stirred for 24 hours in the presence of an excess of potassium phosphate K$_3$PO$_4$. After filtration and evaporation of the solvent, the compound below was obtained:

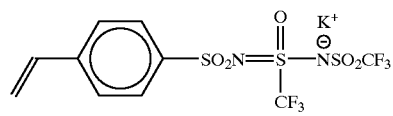

EXAMPLE 15

According to a process similar to that of Example 14, and replacing the p-styrenesulfonamide with allylsulfonamide, the compound below was obtained:

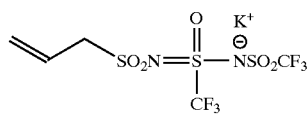

EXAMPLE 16

5 mmol of diphenyliodonium chloride (C$_6$H$_5$)$_2$ICl and 5 mmol of the potassium salt [C$_4$H$_9$SO$_2$N=S(=O)

(CF₃)]₂NK described in Example 12 were stirred together for 24 hours in water. By extracting the aqueous phase with dichloromethane, and after evaporation of the dichloromethane and drying, the compound below was recovered:

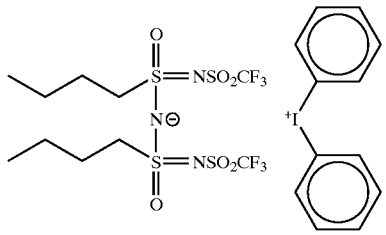

This salt makes it possible to initiate, under the effect of actinic radiation (light, γ-rays, electron beams), cationic polymerization reactions or cationic crosslinking reactions of electron-rich monomers, in particular vinyl ethers, propenyl ethers, epoxides, isobutylene or N-vinylpyrrolidinone.

It is soluble in most common organic solvents (tetrahydrofuran, acetonitrile, dimethylformamide, ethyl acetate, glymes, toluene, etc.) and in aprotic solvating polymers such as polyethylene oxide. It is also soluble to more than 10% by weight in reactive solvents such as triethylene glycol divinyl ether or cyclohexanedimethanol divinyl ether, in contrast, for example, with the bis(trifluoromethanesulfonyl)imide salt of diphenyliodonium.

The photoinitiating properties of this salt were tested by irradiating a solution of triethylene glycol divinyl ether, containing it at 1% by weight, with U.V. radiation at 254 nm, with a power of 1900 mW/cm². After irradiation for a few seconds, the reactive solvent set to a solid, this reaction being highly exothermic.

EXAMPLE 17

The allylsulfonimide of Example 15 was epoxidized by the magnesium salt of commercial peroxyphthalic acid to give the salt:

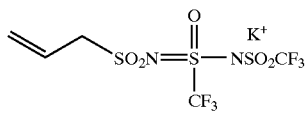

A solution of 100 ml of anhydrous tetrahydrofuran, 50 mmol of said salt and 6 mmol of allyl glycidyl ether were introduced into a Parr®-type chemical reactor. After purging the reactor with argon, 146 mmol of ethylene oxide and then 100 μl of a 10⁻² M solution of potassium t-butoxide in THF were introduced using a valve. The polymerization was then carried out under argon by heating the reaction medium at 60° C. for 48 hours. After cooling, the solution was concentrated and the polymer was then recovered by reprecipitation from ether. After filtration and drying, the potassium cations of this polyelectrolyte were exchanged with lithium cations by passage through a cation-exchange column. The polyelectrolyte below was thus obtained:

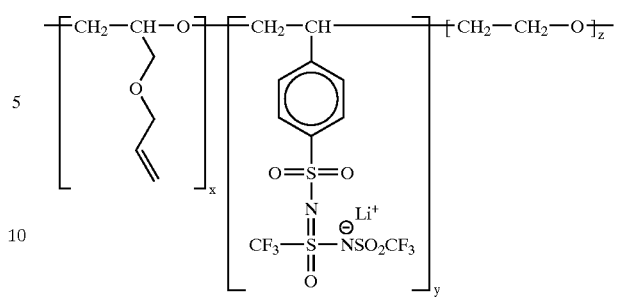

x:y:z being for example 6:50:200 on account of the higher reactivity of ethylene oxide. This polymer makes it possible to prepare polymeric electrolytes or gelled electrolytes containing fixed anions, the polymer fulfilling the double function of a matrix for obtaining the gel and of a polyelectrolyte.

A gelled electrolyte 40 μm in thickness containing (by weight) 30% of the above polyelectrolyte, 35% of ethylene carbonate and 35% of propylene carbonate) was thus prepared, after crosslinking the allyl functions by UV irradiation in the presence of 1,2-diphenyl-1-keto-2,2-dimethoxyethane. This gel has good mechanical properties and a conductivity of greater than $10^{-3}$ S.cm$^{-1}$ at 30° C. The cation-transport number in this electrolyte was estimated at 0.85.

An electrochemical generator was assembled using, as electrolyte, the gelled electrolyte described above. The anode material was a carbon coke (80% by volume) mixed with the copolymer (PANSDTFSI) of this example in non-crosslinked form as binder (20% by volume). The cathode material was a composite material consisting of carbon black (6% by volume), $LiCoNiO_2$ (75% by volume) and non-crosslinked copolymer (PANSDTFSI) (20% by volume). This generator gave good cycling performance at 25° C. It was possible to achieve 1000 charge/discharge cycles between 3 and 4.2 V, preserving a capacitance of greater than 80% of the capacitance at the first cycle. The generator has very good performance during a power demand on account of the use of fixed anions. The use of fixed anions also made it possible to improve the change in the interface resistance.

This family of polymers is of great practical interest for the development of electrochemical generators.

EXAMPLE 18

By ion-exchange in acetone between the potassium salt [C₄H₉SO₂N=S(=O)(CF₃)]₂NK described in Example 12 with 3,3'-diethylthiatricarbocyanine iodide (which is an infrared dye of the cyanine family, sold by Aldrich), followed by a reprecipitation from water, and after filtration and drying, the compound below was obtained:

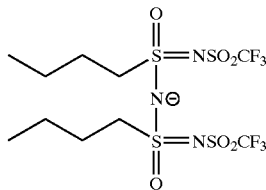

-continued

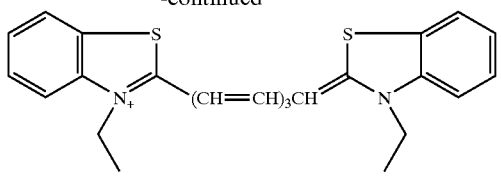

This salt is very soluble in relatively non-polar solvents such as dichloromethane or methylene chloride, as well as in relatively non-polar polymer matrices, such as polymethyl methacrylate.

Moreover, a very pronounced decrease was observed in the aggregation of the cationic dyes with each other on account of the "plasticizing" nature of the di-2-ethylhexylamino groups. This decrease in aggregation is an advantage since the aggregation phenomenon entails a broadening of the optical absorption bands which can prejudice the operating accuracy of systems using dyes, in particular optical data storage disks.

EXAMPLE 19

100 mmol of trimethoxysilane were dissolved in tetrahydrofuran in a three-necked round-bottomed flask equipped with a condenser, a mechanical stirrer and an inlet for neutral gas (Argon); 100 mmol of the potassium salt described in Example 15 and 70 mg of chloroplatinic acid $H_2PtCl_6$ were then added. The mixture was refluxed for 4 hours. After cooling and evaporation of the THF, the compound below was obtained:

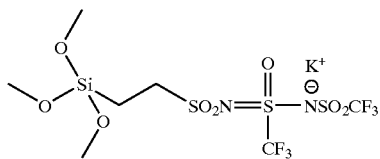

This compound was grafted to the surface of silica particles pretreated in hydrochloric acid solution. Such silica particles are particularly useful for carrying out supported catalysis using a suitable cation.

EXAMPLE 20

10 mmol of the potassium salt $[C_4F_9SO_2N=S(=O)(CF_3)]_2NK$ described in Example 11, were treated with silver tetrafluoroborate in an 80/20 mixture of toluene dioxane. After stirring for a few hours, the reaction medium was filtered to remove the potassium tetrafluoroborate precipitate and anhydrous hydrogen chloride gas in toluene was then bubbled through. After filtration to remove the silver chloride formed, and addition of silica particles, the solvent was evaporated off to give the acid $[C_4F_9SO_2N=S(=O)(CF_3)]_2NH$ deposited on silica. 1 mol of octane and 10 mmol of acid supported on silica were introduced into a Parr reactor and the reactor was then maintained at 200° C for 10 min. The octane was then isomerized into isooctane.

The acid $[C_4F_9SO_2N=S(=O)(CF_3)]_2NH$ deposited on silica and used as isomerization catalyst has an excellent level of use and is easy to recover on account of its low volatility and its oleophobic nature, i.e. its insolubility in aliphatic hydrocarbons.

The acid $[C_4F_9SO_2N=S(=O)(CF_3)]_2NH$ dissolved in fluorinated solvents such as Fluorinert® (sold by the company 3M) can also be used to carry out chemical reactions involving an acidic catalysis in a two-phase medium, the reaction products, which are insoluble in the fluorinated fluid, being recovered by simple separation after settling has taken place.

EXAMPLE 21

10 mmol of the potassium salt $[C_4H_9SO_2N=S(=O)(CF_3)]_2NK$, obtained in Example 12, were stirred in water in the presence of 11 mmol of 1-ethyl-3-methyl-1H-imidazolium chloride (10% excess, sold by Aldrich). A liquid phase denser than water was obtained. This phase was recovered by extraction with dichloromethane. After evaporation of the dichloromethane and drying of the liquid obtained under vacuum at 40° C., the molten salt below was recovered:

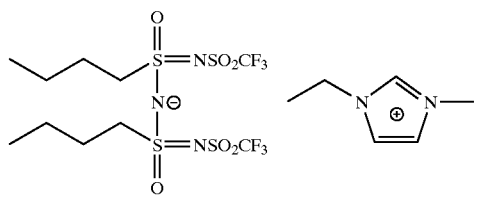

This molten salt has a conductivity of greater than $4.10^{-3}$ $S.cm^{-1}$ and a freezing point of less than −20° C. Its broad redox stability range makes it a particularly advantageous electrolyte for electrochemical generators such as lithium batteries, supercapacitors, light modulation systems and photovoltaic cells.

EXAMPLE 22

10 mmol of the potassium salt $[(CH_3)_2NSO_2N=S(=O)(CF_3)]_2NK$, prepared as in Example 12, were dissolved in 20 ml of THF and were treated with 10 mmol of oxalyl chloride. A precipitate of potassium chloride formed rapidly and was removed by filtration. 5 mmol of $Li_3N$ were then added, under argon, to the filtered solution. After stirring for 48 hours, the solvent was evaporated off and the residue was recrystallized from saturated potassium chloride solution. The compound below was obtained:

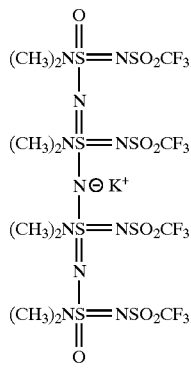

What is claimed is:

1. Ionic compound corresponding to one of the formulae

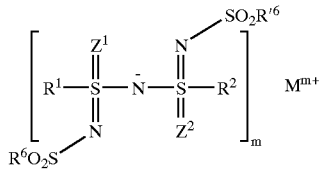

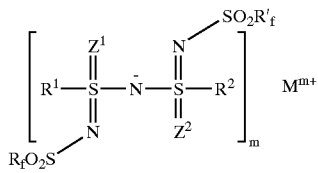

in which:

M$^{m+}$ is a proton or a metal cation having the valency m, chosen from ions of alkali metals, of alkaline-earth metals, of transition metals or of rare-earth metals, or an organic onium cation or an organometallic cation, $1 \leq m \leq 3$;

Z$^1$ and Z$^2$, denoted below by Z$^i$, represent, independently of each other, O, NC≡N, C(C≡N)$_2$, NS(=Z)$_2$R$^6$ or C[S(=Z)$_2$R$^6$]$_2$, Z having the same meaning as Z$^i$.

R$^1$, R$^2$, R$^6$ and R$^{6'}$, denoted below by R$^i$, represent, independently of each other, Y, YO—, YS—, Y$_2$N— or F;

R$_f$, and R$_f'$ represent a perfluoroalkyl radical;

Y represents a monovalent organic radical chosen from alkyl, alkenyl, oxaalkyl, oxaalkenyl, azaalkyl, azaalkenyl, aryl, alkylaryl or perfluoroalkyl radicals, or from the radicals obtained from the abovementioned radicals by substitution, in the chains and/or the aromatic part, with hetero atoms chosen from halogens, oxygen, nitrogen, sulfur or phosphorus; with the proviso that if said heteroatoin is sulfur or phosphorus, said sulfur or phosphorus atom can optionally be in the form of a —SO— group, a —SO$_2$ group or a >PO— group, or alternatively Y is a repeating unit of a polymeric backbone, wherein the cation M$^{m+}$ is an organometallic cation chosen from metallocenium ions, metal cations coordinated by O, S, Se, N, P or As atoms and borne by organic molecules, trialkylsilyl, tetraalkylgermanyl or dialkylstannyl groups in which the alkyl radicals contain from 1 to 10 carbon atoms, and wherein the organometallic cation forms part of a polymer chain.

2. Ionic compound corresponding to one of the formulae

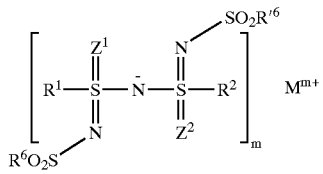

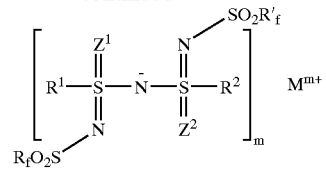

in which:

M$^{m+}$ is a proton or a metal cation having the valency m, chosen from ions of a alkali metals, of alkaline-earth metals, of transition metals or of rare-earth metals, or an organic onium cation or an organometallic cation, $1 \leq m \leq 3$;

Z$^1$ and Z$^2$, denoted below by Z$^i$, represent, independently of each other, O, NC≡N, C(C≡N)$_2$, NS(=Z)$_2$R$^6$ or C[S(=Z)$_2$R$^6$]$_2$, Z having the same meaning as Z$^i$, R$^1$, R$^2$, R$^6$ and R$^{6'}$, denoted below by R$^i$, represent, independently of each other, Y, YO—, YS—, Y$_2$N— or F;

R$_f$ and R$_f'$ represent a perfluoroalkyl radical;

Y represents a monovalent organic radical chosen from alkyl, alkenyl, oxaalkyl, oxaalkenyl, azaalkyl, azaalkenyl, aryl, alkylaryl or perfluoroalkyl radicals, or from the radicals obtained from the abovementioned radicals by substitution, in the chains and/or the aromatic part, with hetero atoms chosen from halogens, oxygen, nitrogen, sulfur or phosphorus; with the proviso that if said heteroatom is sulfur or phosphorus, said sulfur or phosphorus atom can optionally be in the form of a —SO— group, a —SO$^2$ group or a >PO— group, or alternatively Y is a repeating unit of a polymeric backbone, wherein the cation M+ is the repeating unit of a conjugate polymer in cationic oxidized form.

3. Ionic compound corresponding to the formula [R$^1$SO$_2$N—S*=O(R$^2$)=NSO$_2$R$^6$]$_m$M$^{m+}$ in which:

M$^{m+}$ is a proton or a metal cation having the valency m, chosen from ions of at alkali metals, of alkaline-earth metals, of transition metals or of rare-earth metals, or an organic onium cation or an organometallic cation, $1 \leq m \leq 3$;

R$^1$, R$^2$, and R$^6$, denoted below by R$^i$, represent, independently of each other, Y, YO—, YS—, Y$_2$N— or F; with the provision that R$^1$ is different from R$^6$;

Y represents a monovalent organic radical chosen from alkyl, alkenyl, oxaalkyl, oxaalkenyl, azaalkyl, azaalkenyl, aryl, alkylaryl or perfluoroalkyl radicals, or from the radicals obtained from the abovementioned radicals by substitution, in the chains and/or the aromatic part, with hetero atoms chosen from halogens, oxygen, nitrogen, sulfur or phosphorus; with the proviso that if said heteroatom is sulfur or phosphorus, said sulfur or phosphorus atom can optionally be in the form of a —SO— group, a —SO$_2$ group or a >PO— group, or alternatively Y is a repeating unit of a polymeric backbone, wherein the organometallic cation forms part of a polymer chain.

4. Ionic compound corresponding to the formula [R$^1$SO$_2$N—S*=O(R$^2$)=NSO$_2$R$^6$]$_m$M$^{m+}$ in which:

M$^{m+}$ is a proton or a metal cation having the valency m, chosen from ions of at alkali metals, of alkaline-earth metals, of transition metals or of rare-earth metals, or an organic onium cation or an organometallic cation, $1 \leq m \leq 3$;

$R^1$, $R^2$, and $R^6$, denoted below by $R^i$, represent, independently of each other, Y, YO—, YS—, $Y_2N$— or F; with the provision that $R^1$ is different from $R^6$;

Y represents a monovalent organic radical chosen from alkyl, alkenyl, oxaalkyl, oxaalkenyl, azaalkyl, azaalkenyl, aryl, alkylaryl or perfluoroalkyl radicals, or from the radicals obtained from the abovementioned radicals by substitution, in the chains and/or the aromatic part, with hetero atoms chosen from halogens, oxygen, nitrogen, sulfur or phosphorus; with the proviso that if said heteroatom is sulfur or phosphorus, said sulfur or phosphorus atom can optionally be in the form of a —SO— group, a —$SO_2$ group or a >PO— group, or alternatively Y is a repeating unit of a polymeric backbone, wherein the cation $M^+$ is the repeating unit of a conjugate polymer in cationic oxidized form.

* * * * *